United States Patent
Stubbs et al.

(10) Patent No.: US 8,639,331 B2
(45) Date of Patent: Jan. 28, 2014

(54) SYSTEMS AND METHODS FOR PROVIDING ARRHYTHMIA THERAPY IN MRI ENVIRONMENTS

(75) Inventors: Scott R. Stubbs, Maple Grove, MN (US); James O. Gilkerson, Stillwater, MN (US); Diane Schuster, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 913 days.

(21) Appl. No.: 12/639,848

(22) Filed: Dec. 16, 2009

(65) Prior Publication Data

US 2010/0211123 A1    Aug. 19, 2010

Related U.S. Application Data

(60) Provisional application No. 61/153,708, filed on Feb. 19, 2009.

(51) Int. Cl.
*A61N 1/00* (2006.01)
(52) U.S. Cl.
USPC ............................................................ 607/15
(58) Field of Classification Search
USPC ............................................................ 607/15
See application file for complete search history.

(56) References Cited

U.S. PATENT DOCUMENTS

| | | | |
|---|---|---|---|
| 3,888,260 A | 6/1975 | Fischell | |
| 3,898,995 A | 8/1975 | Dresbach | |
| 4,091,818 A | 5/1978 | Brownlee et al. | |
| 4,379,459 A | 4/1983 | Stein | |
| 4,404,125 A | 9/1983 | Abolins et al. | |
| 4,516,579 A | 5/1985 | Irnich | |
| 4,611,127 A | 9/1986 | Ibrahim et al. | |
| 4,694,837 A | 9/1987 | Blakeley et al. | |
| 4,729,376 A | 3/1988 | DeCote, Jr. | |

(Continued)

FOREIGN PATENT DOCUMENTS

| | | |
|---|---|---|
| EP | 0530006 | 3/1993 |
| EP | 0591334 | 4/1994 |

(Continued)

OTHER PUBLICATIONS

Schueler, et al., "MRI Compatibility and Visibility Assessment of Implantable Medical Devices," Journal of Magnetic Resonance Imaging, 9:596-603 (1999).

(Continued)

*Primary Examiner* — Christopher D Koharski
*Assistant Examiner* — Nadia Ahmad
(74) *Attorney, Agent, or Firm* — Faegre Baker Daniels LLP

(57) ABSTRACT

Systems and methods for arrhythmia therapy in MRI environments are disclosed. Various systems disclosed utilize ATP therapy rather than ventricular shocks when patients are subjected to electromagnetic fields in an MRI scanner bore and shock therapy is not available. As the patient is moved out from within the scanner bore and away from the MRI scanner, the magnetic fields diminish in strength eventually allowing a high voltage capacitor within the IMD to charge if necessary. The system may detect when the electromagnetic fields no longer interfere with the shock therapy and will transition the IMD back to a normal operational mode where shock therapy can be delivered. Then, if the arrhythmia still exists, the system will carry out all of the system's prescribed operations, including the delivery of electric shocks to treat the arrhythmia.

21 Claims, 5 Drawing Sheets

(56) References Cited

U.S. PATENT DOCUMENTS

| | | |
|---|---|---|
| 4,751,110 A | 6/1988 | Gulla et al. |
| 4,779,617 A | 10/1988 | Whigham |
| 4,823,075 A | 4/1989 | Alley |
| 4,869,970 A | 9/1989 | Gulla et al. |
| 4,934,366 A | 6/1990 | Truex et al. |
| 5,038,785 A | 8/1991 | Blakeley et al. |
| 5,075,039 A | 12/1991 | Goldberg |
| 5,076,841 A | 12/1991 | Chen et al. |
| 5,120,578 A | 6/1992 | Chen et al. |
| 5,181,511 A | 1/1993 | Nickolls et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsilik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,990 A | 8/1995 | Wahlstrand et al. |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukrup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,662,697 A | 9/1997 | Li et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,241 A | 7/1998 | Felblinger et al. |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappoholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spher |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 | 9/2005 | Zeijlemaker et al. |

(56) References Cited

U.S. PATENT DOCUMENTS

| | | |
|---|---|---|
| 6,963,779 B1 | 11/2005 | Shankar |
| 7,013,180 B2 | 3/2006 | Villaseca et al. |
| 7,020,517 B2 | 3/2006 | Weiner |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 * | 1/2007 | Kroll et al. ............ 607/36 |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,801,625 B2 | 9/2010 | MacDonald |
| 7,835,803 B1 | 11/2010 | Malinowski et al. |
| 7,839,146 B2 | 11/2010 | Gray |
| 8,014,867 B2 * | 9/2011 | Cooke et al. ............ 607/31 |
| 8,032,228 B2 | 10/2011 | Ameri et al. |
| 8,086,321 B2 | 12/2011 | Ameri |
| 8,121,705 B2 | 2/2012 | MacDonald |
| 8,160,717 B2 | 4/2012 | Ameri |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton, Jr. et al. |
| 2002/0166618 A1 | 11/2002 | Wolf et al. |
| 2002/0175782 A1 | 11/2002 | Trihn et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton, Jr. et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1 | 3/2004 | Larson et al. |
| 2004/0088012 A1 | 5/2004 | Kroll et al. |
| 2004/0093432 A1 | 5/2004 | Luo et al. |
| 2004/0263174 A1 | 12/2004 | Gray et al. |
| 2005/0043761 A1 | 2/2005 | Connelly et al. |
| 2005/0070787 A1 | 3/2005 | Zeijlemaker |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0173295 A1 | 8/2006 | Zeijlemaker |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0019354 A1 | 1/2007 | Kamath |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |

(56) References Cited

U.S. PATENT DOCUMENTS

| | | |
|---|---|---|
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0154342 A1 | 6/2008 | Digby et al. |
| 2008/0221638 A1 | 9/2008 | Wedan et al. |
| 2008/0234772 A1* | 9/2008 | Shuros et al. .................. 607/11 |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0157146 A1 | 6/2009 | Linder et al. |
| 2009/0204182 A1 | 8/2009 | Ameri |
| 2009/0210025 A1 | 8/2009 | Ameri |
| 2010/0087892 A1 | 4/2010 | Stubbs et al. |
| 2011/0137359 A1 | 6/2011 | Stubbs et al. |
| 2011/0270338 A1 | 11/2011 | Cooke et al. |
| 2011/0276104 A1 | 11/2011 | Ameri et al. |
| 2012/0071941 A1 | 3/2012 | Ameri |
| 2012/0253425 A1 | 10/2012 | Yoon et al. |

FOREIGN PATENT DOCUMENTS

| | | |
|---|---|---|
| EP | 0705621 | 4/1996 |
| EP | 0719570 | 7/1996 |
| EP | 0836413 | 4/1998 |
| EP | 0331959 | 9/1998 |
| EP | 0870517 | 10/1998 |
| EP | 0891207 | 1/1999 |
| EP | 0891786 | 1/1999 |
| EP | 0980105 | 2/2000 |
| EP | 0989623 | 3/2000 |
| EP | 0989624 | 3/2000 |
| EP | 1007132 | 6/2000 |
| EP | 1007140 | 6/2000 |
| EP | 1060762 | 12/2000 |
| EP | 1061849 | 12/2000 |
| EP | 1109180 | 6/2001 |
| EP | 1128764 | 9/2001 |
| EP | 1191556 | 3/2002 |
| EP | 1271579 | 1/2003 |
| EP | 1308971 | 5/2003 |
| EP | 1372782 | 1/2004 |
| WO | WO 91/04069 | 4/1991 |
| WO | WO 96/38200 | 12/1996 |
| WO | WO 97/12645 | 4/1997 |
| WO | WO 00/54953 | 9/2000 |
| WO | WO 01/37286 | 5/2001 |
| WO | WO 01/80940 | 11/2001 |
| WO | WO 01/86774 | 11/2001 |
| WO | WO 02/056761 | 7/2002 |
| WO | WO 02/065895 | 8/2002 |
| WO | WO 02/072004 | 9/2002 |
| WO | WO 02/089665 | 11/2002 |
| WO | WO 02/092161 | 11/2002 |
| WO | WO 03/013199 | 2/2003 |
| WO | WO 03/037399 | 5/2003 |
| WO | WO 03/059445 | 7/2003 |
| WO | WO 03/061755 | 7/2003 |
| WO | WO 03/063946 | 8/2003 |
| WO | WO 03/063952 | 8/2003 |
| WO | WO 03/063954 | 8/2003 |
| WO | WO 03/063955 | 8/2003 |
| WO | WO 03/063956 | 8/2003 |
| WO | WO 03/063958 | 8/2003 |
| WO | WO 03/063962 | 8/2003 |
| WO | WO 03/070098 | 8/2003 |
| WO | WO 03/073449 | 9/2003 |
| WO | WO 03/073450 | 9/2003 |
| WO | WO 03/086538 | 10/2003 |
| WO | WO 03/090846 | 11/2003 |
| WO | WO 03/090854 | 11/2003 |
| WO | WO 03/095022 | 11/2003 |
| WO | WO 2006/124481 | 11/2006 |

OTHER PUBLICATIONS

Bruce L. Wilkoff, et al., "A Comparison of Empiric to Physician-Tailored Programming of Implantable Cardioverter-Defibrillators Results From the Prospective Randomized Multicenter EMPIRIC Trial," Journal of the American College of Cardiology vol. 48, No. 2, 2006. doi:10.1016/j.jacc.2006.03.037.

Michael O. Sweeney, et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock ThErapies (PainFREE Rx II) Trial, American Heart Association, 2005.

Martha Kerr, Shock Rate Cut 70% With ICDs Programmed to First Deliver Antitachycardia Pacing: Results of the PainFREE Rx II Trial, Medscape CRM News, May 21, 2003.

International Search Report and Written Opinion issued in PCT/US2009/068314, mailed Mar. 25, 2009, 14 pages.

Dempsey Mary F. et al., "Investigation of the Factors Responsible for Burns During MRI", *Journal of Magnetic Resonance Imaging* 2001;13:627-631.

Luechinger, Roger et al., "In vivo heating of pacemaker leads during magnetic resonance imaging", *European Heart Journal* 2005;26:376-383.

Shellock, Frank G. et al., "Cardiovascular catheters and accessories: ex vivo testing of ferromagnetism, heating, and artifacts associated with MRI", *Journal of Magnetic Resonance Imaging*, Nov./Dec. 1998; 8:1338-1342.

Shellock FG, "Reference manual for magnetic resonance safety, implants, and devices", pp. 136-139, 2008 ed. Los Angeles; Biomedical Research Publishing Group; 2008.

Hebrank FX, Gebhardt M. SAFE model: a new method for predicting peripheral nerve stimulations in MRI (abstr) In: Proceedings of the Eighth Meeting of the International Society for Magnetic Resonance in Medicine. Berkeley, Calif: International Society for Magnetic Resonance in Medicine, 2000; 2007.

International Search Report and Written Opinion issued in PCT/US2010/053202, mailed Dec. 30, 2010, 12 pages.

Nyenhuis, John A. et al., "MRI and Implantable Medical Devices: Basic Interactions With an Emphasis on Heting", IEEE Transactions on Device and Materials Reliability, vol. 5, No. Sep. 2005, pp. 467-480.

* cited by examiner

SYSTEMS AND METHODS FOR PROVIDING ARRHYTHMIA THERAPY IN MRI ENVIRONMENTS

CROSS-REFERENCE TO RELATED APPLICATIONS

This application claims the benefit of U.S. Provisional Application No. 61/153,708, filed on Feb. 19, 2009, which is hereby incorporated by reference for all purposes in its entirety.

TECHNICAL FIELD

Various embodiments of the present invention generally relate to implantable medical devices. More specifically, embodiments of the present invention relate to systems and methods for providing arrhythmia therapy in MRI environments.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator such as a pacemaker, an implantable cardiac defibrillator, or a cardiac resynchronization (CRT) device. Such devices are typically coupled to a number of conductive leads having one or more electrodes that can be used to deliver pacing therapy and/or electrical shocks to the heart. In atrioventricular (AV) pacing, for example, the leads are usually positioned in a ventricle and atrium of the heart, and are attached via lead terminal pins to a pacemaker or defibrillator which is implanted pectorally or in the abdomen.

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may interfere with the operation of the pulse generator and leads. In some cases, for example, the presence of strong magnetic fields and RF energy during an MRI scan may prevent the charging of a high voltage capacitor within the pulse generator, which can affect the ability of the pulse generator to deliver electrical shocks to the patient when an event such as a tachyarrhythmia occurs. In other cases, the RF energy and/or time varying gradient fields may prevent the sensing and detection of tachyarrhythmias.

SUMMARY

Various embodiments of the present invention generally relate to implantable medical devices (IMD). More specifically, embodiments of the present invention relate to systems and methods for providing arrhythmia therapy in MRI environments.

Some embodiments provide for a method of operating an IMD in the presence of an MRI environment or other environment with strong electromagnetic fields. According to various embodiments, the IMD is capable of operating in a variety of operational modes. Examples of operational modes include, but are not limited to, a normal mode, a tachy therapy mode, an MRI mode, an MRI mode stat therapy state, and an antitachyarrhythmia therapy pacing (ATP) mode.

When a patient with an IMD enters the presence of an MRI environment, the IMD is placed from its normal operation mode into a first operational mode (e.g., an MRI mode), which adjusts one or more settings within the IMD to adjust the operation of the IMD when exposed to an MRI electromagnetic field. In some embodiments, the transition from the normal operation mode to the first operational mode may cause the IMD to deactivate one or more sensors, or alternatively, to ignore the signals received from the sensors, which are normally used to sense various electrical parameters within the body. According to various embodiments, the IMD can be placed in the first operational mode in response to a command received from an external device.

In some embodiments, the IMD automatically detects the presence of the electromagnetic fields that would saturate the power supply ferromagnetic components resulting in an inability of the IMD to charge the high voltage capacitor to a sufficient level for delivering shock therapy before a maximum charging time has been reached. In some embodiments, a core saturation signal is generated (e.g., internally and/or externally to the IMD) to indicate the presences of an electromagnetic field that would saturate the power supply ferromagnetic components. The IMD can monitor for the core saturation signal and initiate a transition to the first operational mode automatically.

In various embodiments of the first operational mode, one or more sensors are deactivated or the inputs from those sensors are ignored. In this mode, an operator operating the MRI scanner monitors the patient for potential distress within the scanner. If the operator determines that the patient is in distress, then the operator stops the MRI and uses an external device, such as a programmer, a device communicator, an MRI communicator, an MRI partner, a personal computer with a telemetry device, an MRI scanner controller with a telemetry device, or other device to transmit a command (e.g., a stat therapy command) to the IMD indicating the need to provide immediate therapy to the patient from the IMD.

A device communicator, for example, can be an external device that links implanted devices with one or more patient management systems. According to some embodiments, the device communicator is an electronic device that uses RF to interrogate the implanted PG on either a scheduled basis or ad hoc basis and then transmits the retrieved information to the patient management system that collects, processes and reports on the retrieved information to physicians.

According to some embodiments, the command can be received from the external device using RF, acoustic, or other wireless communications while the IMD is operating in a first operational mode (e.g., an MRI mode). Once the command is received by the IMD, the IMD then enters a second operational mode (e.g., an MRI mode stat therapy state). In some embodiments, upon entering the second operational mode one or more sensors associated with the IMD are reactivated. In those embodiments where the sensors are not deactivated during the first operational mode, the IMD no longer ignores signals from the sensors. Using the input from the sensors, the IMD determines whether a tachyarrhythmia or other cardiac episode or condition is present.

If during the second operation mode the IMD determines that no tachyarrhythmia is present, the IMD is configured to return to the first operational mode, and in some embodiments deactivates the one or more sensors or, alternatively, ignores the signals received from the sensors. If, however, a tachyarrhythmia is present, then the IMD can be configured to deliver antitachyarrhythmia pacing (ATP) therapy to the patient. In some embodiments, the ATP therapy may start with higher pacing rates in earlier programmed intervals and decreasing pacing rates in subsequent intervals. In accordance with various embodiments, only a maximum number of ATP sessions (e.g., two sessions, three sessions, four sessions, five sessions, etc.) will be delivered in the second operational mode.

While delivering ATP therapy, some embodiments of the IMD monitor a core saturation signal to determine when the IMD is out of the strong magnetic fields created by the MRI device. Once the IMD is outside of the field, the IMD can enter a third operational mode (e.g., a normal mode of operation) where the IMD determines if tachy therapy is needed. If a determination is made that tachy therapy is needed, the IMD may enter a fourth operational mode (e.g., a tachy therapy mode) to deliver shock therapy and/or pacing therapy.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
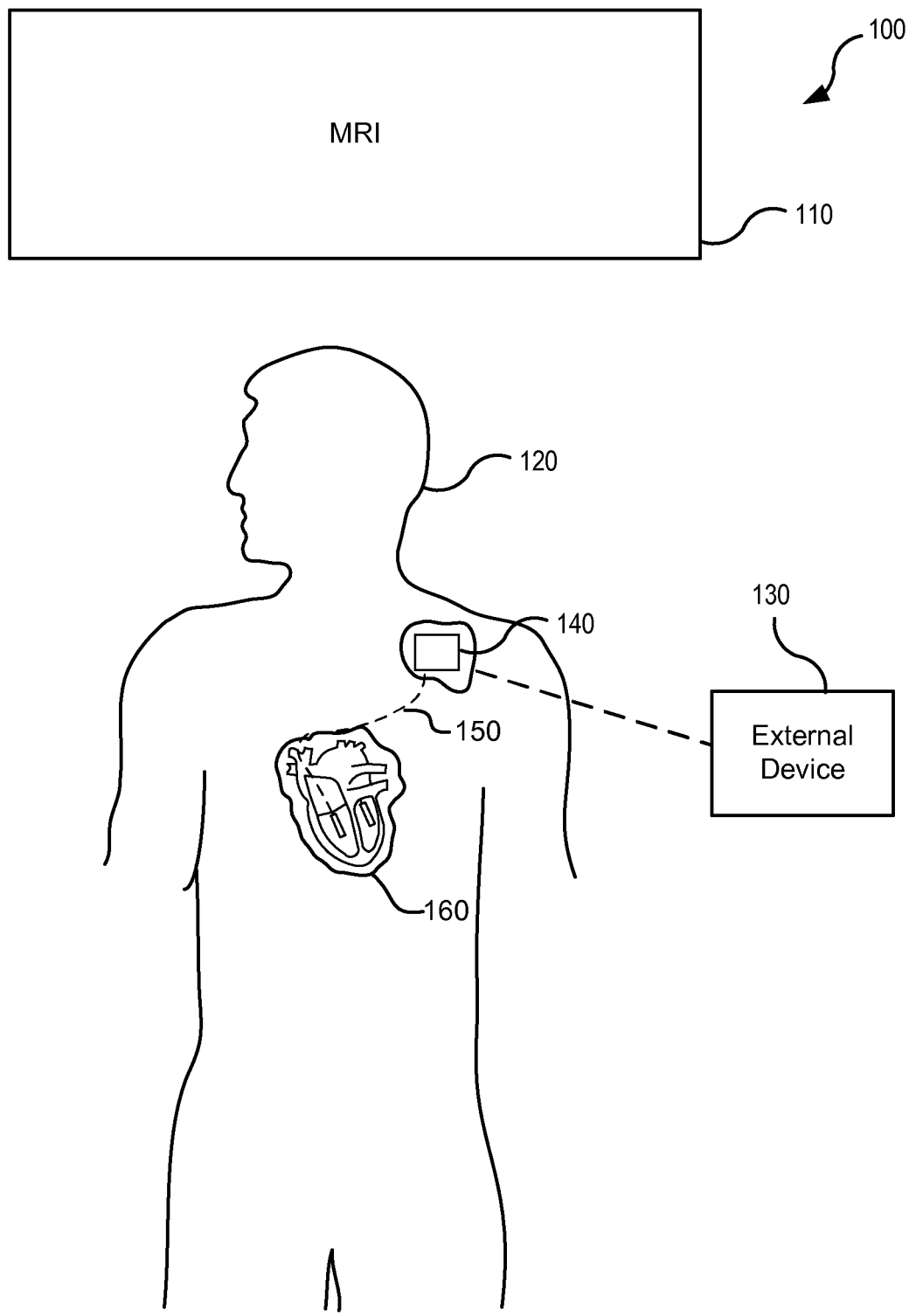
FIG. 1 illustrates an MRI scanner and an IMD implanted within a torso of a human patient according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

MRI scanners present complex electromagnetic fields that interfere with tachyarrhythmia detection and therapy. In addition, RF and gradient magnetic fields present significant electromagnetic energy that can affect the sense passband of a pulse generator. As a result, during MRI imaging of an individual with an IMD, the electromagnetic radiation produced by the MRI scanner may interfere with the operation of various components of an IMD. Consequently, the IMD may be unable to discriminate cardiac signals from electromagnetic interference (EMI).

For example, electromagnetic radiation is known to affect the operation of pulse generators and leads. In some cases, the presence of strong magnetic fields, such as a large B0 magnetic field and RF energy during an MRI scan may prevent the charging of a high voltage capacitor within the pulse generator by saturating the power supply's ferromagnetic components, which can result in an inability to charge the high voltage capacitor to a stat shock level before a charge timeout occurs. Consequently, the saturation can affect the ability of the pulse generator to deliver electrical shocks to the patient when an event such as a tachyarrhythmia occurs.

Some embodiments provide for a method of operating an IMD in the presence of an MRI environment. In particular, various embodiments provide a way to utilize antitachyarrhythmia pacing (ATP) therapy rather than ventricular shocks when the patient is in an MRI scanner bore. As the patient is moved away from the scanner, due to the emergency, the magnetic fields (e.g., large B0 magnetic fields) diminish in strength eventually permitting the power supply to recharge the high voltage capacitor within the IMD, if necessary. Various embodiments of the system will detect when the fields no longer interfere with the shock therapy and will transition the IMD back to a normal operational mode. Then, if the arrhythmia still exists, the IMD will carry out all of the system's prescribed operations, including the delivery of shocks if programmed, to treat the arrhythmia.

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

While, for convenience, some embodiments are described with reference to treating ventricular tachyarrhythmia using an IMD, embodiments of the present invention may be applicable to various other physiological measurements, treatments, and IMD devices. As such, the applications discussed herein are not intended to be limiting, but instead exemplary. Other systems, devices, and networks to which embodiments are applicable include, but are not limited to, other types of sensory systems, medical devices, medical treatments, and computer devices and systems. In addition, various embodiments are applicable to all levels of sensory devices from a single IMD with a sensor to large networks of sensory devices.

FIG. 1 illustrates a magnetic resonance imaging (MRI) scanner 110 and an implantable medical device (IMD) implanted within a torso of a human patient 120 according to various embodiments. One or more external devices 130 are capable of communicating with an implantable medical device (IMD) (e.g., a cardiac rhythm management device) implanted within the patient 120. In the embodiment shown in FIG. 1, the IMD includes a pulse generator (PG) 140 and a lead 150. However, in other embodiments other components or IMD devices can be used with or without the PG 140 and/or lead 150. During normal device operation, the pulse generator 140 is configured to deliver electrical therapeutic stimulus to the patient's heart 160 for providing tachycardia ventricular fibrillation, anti-bradycardia pacing, anti-tachycardia pacing, and/or other types of therapy.

As illustrated in FIG. 1, the IMD includes a PG 140 such as a pacemaker, a cardiac defibrillator, cardiac resynchronization therapy device, or a neural stimulator. The PG 140 can be implanted pectorally within the body, typically at a location such as in the patient's chest. In some embodiments, PG 140 can be implanted in or near the abdomen.

The system may also include one or more remote terminals or external devices 130 (e.g., a computing device and/or programming device), which may communicate with the PG 140 from a location outside of the patient's body. According to various embodiments, external device 130 can be any device external to the patient's body that is telemetry enabled and capable of communicating with the IMD 140. Examples of external devices can include, but are not limited to, programmers (PRM), in-home monitoring devices, personal computers with telemetry devices, MRI scanner with a telemetry device, manufacturing test equipment, or wands. In some embodiments, the PG 140 communicates with the remote terminal 130 via a wireless communication interface. Examples of wireless communication interfaces can include, but are not limited to, radio frequency (RF), inductive, and acoustic telemetry interfaces.

Figure 2:
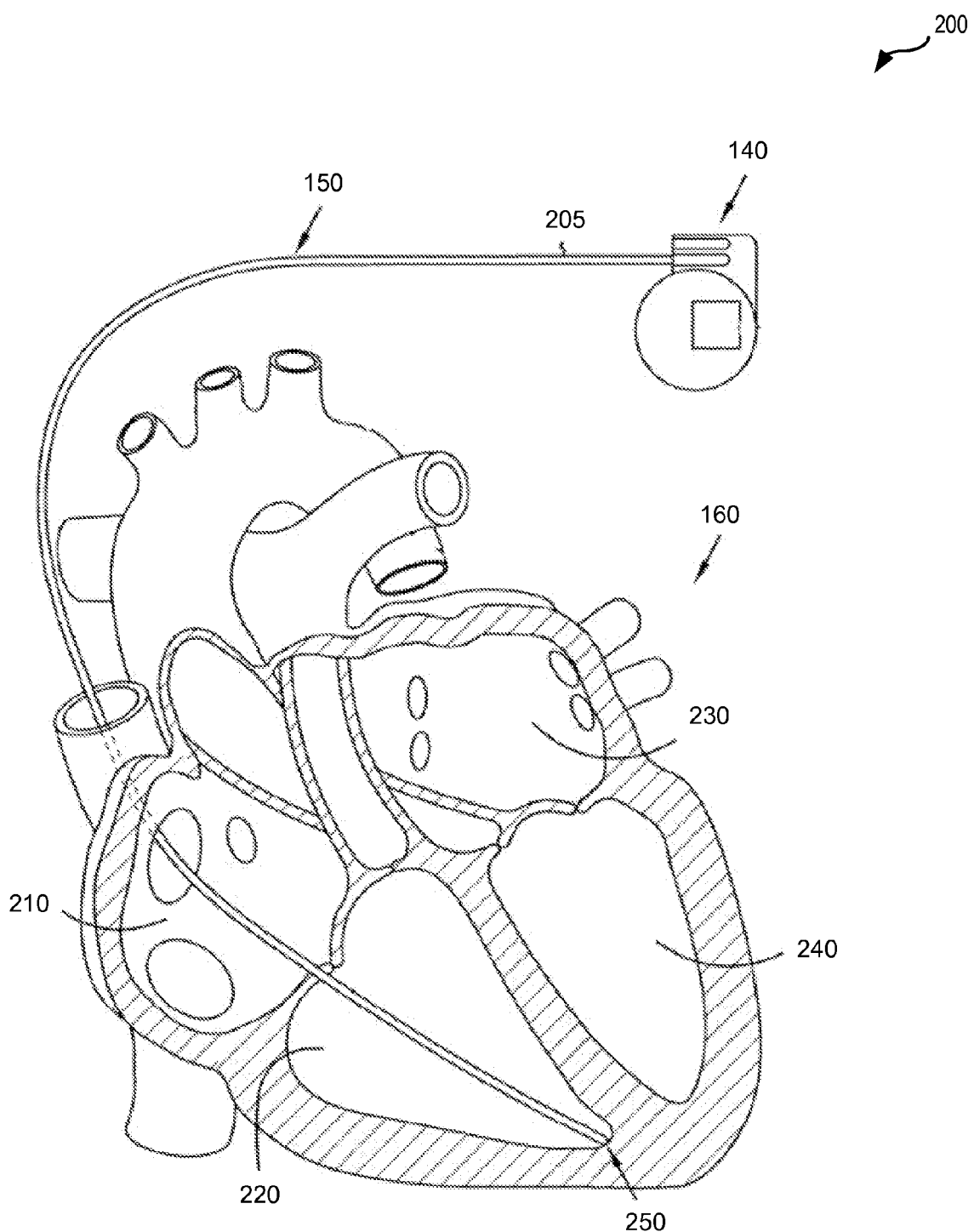
FIG. 2 is a schematic view of an illustrative pulse generator and lead implanted within the body of a patient which may be used in accordance with some embodiments of the present invention.

FIG. 2 is a schematic view of a cardiac rhythm management system 200 including an illustrative medical device 140 equipped with a lead implanted within the body of a patient. In the embodiment depicted, medical device 140 comprises a pulse generator implanted within the body. The medical device includes a lead 150 placed in the patient's heart 160. According to various embodiments, lead 150 can be a tachy lead. However, in other embodiments, other types of leads can be used. The heart 160 includes a right atrium 210, a right ventricle 220, a left atrium 230, and a left ventricle 240.

A proximal portion 205 of the lead 150 can be coupled to or formed integrally with the pulse generator 140. A distal portion 250 of the lead 150, in turn, can be implanted at a desired location within the heart 160 such as in the right ventricle 220, as shown. Although the illustrative embodiment depict only a single lead 150 inserted into the patient's heart 160, in other embodiments multiple leads can be utilized so as to electrically stimulate other areas of the heart 160. In some embodiments, for example, the distal portion of a second lead (not shown) may be implanted in the right atrium 210. In addition, or in lieu, another lead may be implanted at the left side of the heart 160 (e.g., in the coronary veins, the left ventricle, etc.) to stimulate the left side of the heart 160. Other types of leads such as epicardial leads may also be utilized in addition to, or in lieu of, the lead 150 depicted in FIGS. 1-2.

During operation, the lead 150 can be configured to convey electrical signals between the heart 160 and the pulse generator 140. For example, in those embodiments where the pulse generator 140 is a pacemaker, the lead 150 can be utilized to deliver electrical therapeutic stimulus for pacing the heart 160. In those embodiments where the pulse generator 140 is an implantable cardiac defibrillator, the lead 150 can be utilized to deliver electric shocks to the heart 160 in response to an event such as a ventricular fibrillation. In some embodiments, the pulse generator 140 includes both pacing and defibrillation capabilities.

Figure 3:
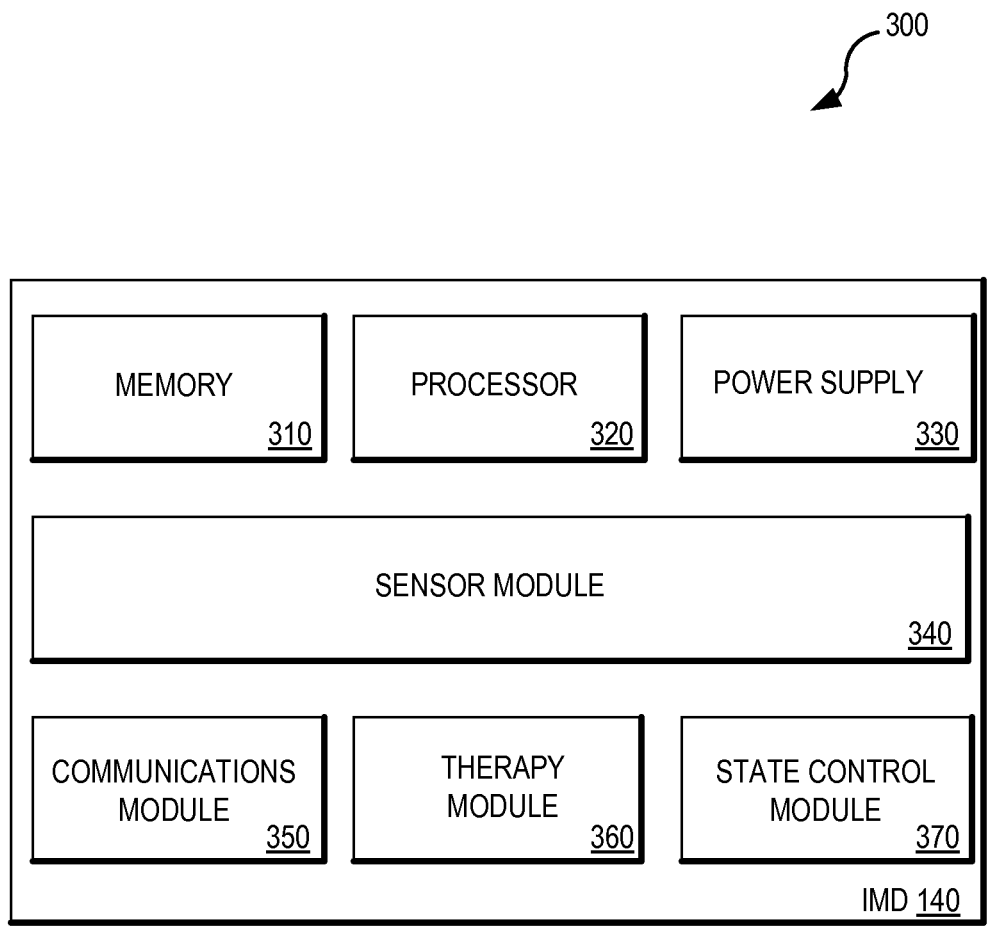
FIG. 3 is a block diagram illustrating several exemplary components of an implantable medical device (IMD), such as a pulse generator, in accordance with one or more embodiments of the present invention.

FIG. 3 is a block diagram 300 illustrating several exemplary components of an implantable medical device (IMD) 140, such as a pulse generator, in accordance with one or more embodiments. As shown in FIG. 3, IMD 140 includes a memory 310, a processor 320, a power supply 330, a sensor module 340, a communications module 350, a therapy module 360, and a state control module 370. Other embodiments may include some, all, or none of these modules along with other modules or application components. For example, some embodiments may include signal filtering and analysis modules. Still yet, various embodiments may incorporate two or more of these modules into a single module and/or associate a portion of the functionality of one or more of these modules with a different module. For example, in various embodiments, therapy module 360 and state control module 370 may be combined into a single control module.

According to various embodiments, pulse generator 140 generates pacing and/or shock pulses and receives electrical signals from the heart through lead 150 (or multiple leads) and/or other sensor devices. Power supply 330 can be any power supplying device that is capable of providing the necessary power requirements for the pulse generator 140. In some embodiments, power supply 330 is a battery that may or may not be rechargeable. In some cases, the battery typically is not capable of delivering the short burst of high charge that is required of a defibrillation shock. As such, in various embodiments, the pulse generator 140 includes a capacitor (not shown) that charges prior to delivery of a defibrillation shock.

Processor 320 executes instructions stored in the memory 310 or in other modules such as, e.g., sensor module 340, communications module 350, therapy module 360, state control module 370, and/or other modules that may be present. In general, processor 320 executes instructions that cause the processor 320 to control or facilitate the functions of the pulse generator 140 and/or components of the pulse generator 140. Memory 310 can include volatile memory and nonvolatile memory. In accordance with some embodiments, nonvolatile memory can store code that includes bootstrap functions and device recovery operations, such as microprocessor reset. The nonvolatile memory may also include calibration data and parameter data in some embodiments. The volatile memory can include diagnostic and/or microprocessor-executable code, operating parameters, status data, and/or other data.

In some embodiments, sensor module 340 controls sensory systems and monitors data received through the sensors and leads 150. For example, the sensor module may monitor electrical signals from an electrode that could be provided as part of an electrode on a lead. In some embodiments, the data received can be continuously stored in a circular buffer in volatile memory which is part of memory 310. Examples of the type data can include, without limitation, electrogram (EGM) data, marker data, interval data, sensor data, and/or morphology data. In accordance with various embodiments, sensor module 340 can use diagnostic data to determine whether various irregular cardiac episodes are occurring. A cardiac episode is any detectable heart condition or behavior of interest. By way of example, but not limitation, episodes such as arrhythmias can be detected, either atrial or ventricular, including tachycardia, bradycardia, or fibrillation.

According to the operational mode of the IMD, sensor module 340 may activate and/or deactivate one or more sensors or sensory systems. In some embodiments, sensor module 340 will ignore data received from the sensors when the IMD is in certain operational modes (e.g., MRI mode), as discussed further herein.

Episodes such as tachyarrhythmia can trigger attempts to deliver therapy through therapy module 360, and also trigger storage of diagnostic data related in time to the episodes and the delivery of the therapy. Cardiac episodes and therapy delivery attempts are both examples of these types of events. Although embodiments described herein relate to cardiac episodes, it is to be understood that the invention is not limited to cardiac episodes or events, but may be beneficially applied to other types of events and episodes, including, but not limited to, low blood sugar episodes, neurological episodes, temperature episodes, or others.

In some embodiments, therapy module 360 can deliver pacing therapy and/or shock therapy to restore normal operation of heart 160. For example, the pacing therapy can include antitachyarrhythmia pacing therapy (ATP) for only a limited number of sessions (e.g., a maximum of five sessions). The pacing threshold is generally highest for the initial session with diminished pacing occurring with each additional session.

According to various embodiments, communications module 350 provides communication functionality so that the IMD 140 can communicate with an external device. In some embodiments, communications module 350 telemeters requested data to the external device wirelessly using any number of suitable wireless communication modes, such as magnetic, radio frequency, and/or acoustic. As such, through communications module 350, an external device can obtain diagnostic data stored in memory 310, such as, but not limited to, electrogram (EGM) data, marker data, and therapy administration data.

In addition to transmitting information, communications module 350, according to various embodiments, monitors for various external commands. In some embodiments, the external commands include, but are not limited to, an MRI mode command, a stat therapy command, a stat shock command, and/or the like. When one or more IMD operational mode commands are received, the communications module 350 can transmit the command(s) to state control module 370 which will transition between the various operational modes.

In accordance with various embodiments, state control module 370 is adapted to place the IMD into one of the following states: a normal operation mode, a tachy therapy mode, an MRI mode, an MRI mode stat therapy state, and an antitachyarrhythmia therapy (ATP) delivery mode. The transitions between these modes and the IMD operational features are described in more detail in FIG. 4.

Figure 4:
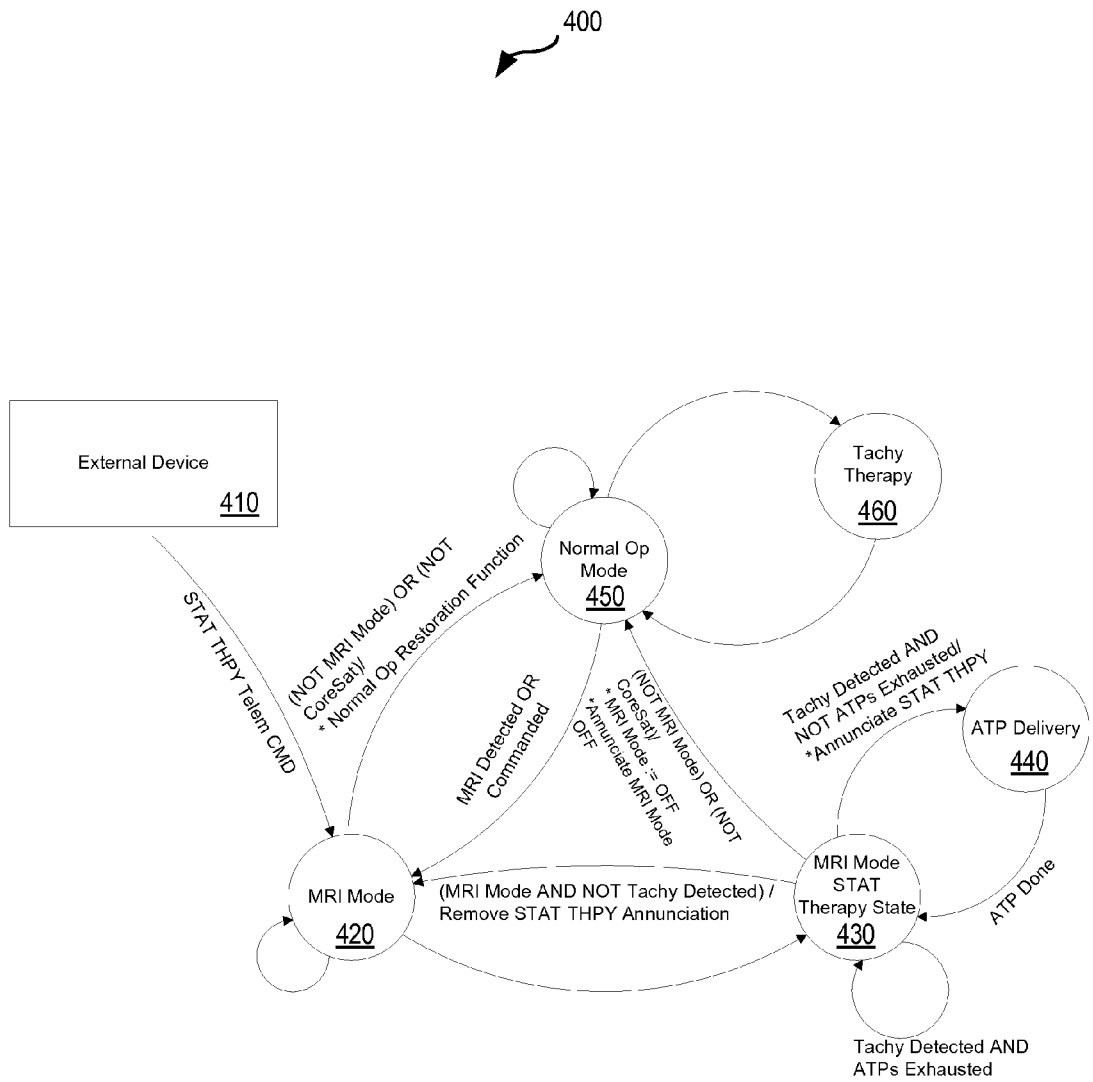
FIG. 4 is a state flow diagram illustrating exemplary operational modes of an implantable medical device in accordance with various embodiments of the present invention.

FIG. 4 is a state flow diagram 400 illustrating exemplary operational modes of an implantable medical device in accordance with various embodiments. As shown in FIG. 4, when a patient with the IMD enters the presence of an MRI environment, the IMD is transitioned from a normal operation mode into an MRI operation mode 420. This can be done in a variety of ways. For example, in some embodiments, an MRI command is received from external device 410 through communications module 350. The command is then communicated to state control module 370 which processes the command and places the IMD in the MRI mode 420. In other embodiments, an MRI scan can be automatically detected by monitoring for a saturation of the power supply ferromagnetic components created by the magnetic fields of the MRI.

In MRI mode 420, one or more sensors are deactivated or the inputs from those sensors are ignored. In various embodiments, the sensors are controlled by sensor module 340. While in MRI mode 420, a person operating the MRI scanner monitors the patient for potential distress. If the operator determines that the patient is in distress, then the operator stops the MRI scan and uses external device 410 to transmit a stat therapy command to the IMD. The stat therapy command indicates the need for immediate therapy from the IMD device. According to various embodiments, external device 410 can be, but is not limited to, a programmer, a device communicator, an MRI communicator, an MRI partner, a personal computer with a telemetry device, an MRI scanner controller with a telemetry device, or other devices known to those of ordinary skill in the art.

A device communicator, for example, can be an external device that links implanted devices with one or more patient management systems. According to some embodiments, the device communicator is an electronic device that uses RF to interrogate the implanted PG on either a scheduled basis or ad hoc basis and then transmits the retrieved information to the patient management system that collects, processes and reports on the retrieved information to physicians.

The stat therapy command is then validated in some embodiments, and the IMD enters the MRI mode stat therapy state 430. In accordance with various embodiments, MRI mode stat therapy state 430 changes the state of one or more sensors or sensory systems. For example, in some embodiments, sensing is turned on and a determination is made if a tachyarrhythmia is present through the use of the sensors. If no tachyarrhythmia is determined to be present, no therapy is delivered and the state control module 370 returns the IMD to MRI mode 420.

If a tachyarrhythmia is determined to be present and the antitachyarrhythmia pacing (ATP) has not been exhausted, the state control module 370 will cause the IMD to enter the ATP delivery mode 440. In ATP delivery mode 440, single chamber ventricular demand (VVI) pacing can pace the heart until the pacing captures the heart. Once the pacing captures the heart, the IMD slows the pacing rate gradually. If this pacing does not capture the heart then, at such point, the patient is removed from the MRI scanner allowing the patient to receive shocking therapy from the IMD. Embodiments can provide other types of pacing therapy such as dual chamber pacing therapy.

When the pacing therapy session is complete, state control module 370 returns the IMD to the MRI mode stat therapy state 430. A determination is made as to whether the tachyarrhythmia still exists and the ATP therapy has not been exhausted. If the tachyarrhythmia is still present and the ATP therapy has not been exhausted the control module 370 will cause the IMD to enter the ATP delivery mode 440 again to provide another ATP therapy session to the patient. This process continues until the ATP sessions are exhausted, or until the tachyarrhythmia is no longer determined to be present. If a determination is made that the sessions are exhausted, then the state control module 370 will cause the IMD to remain in MRI mode stat therapy state 430.

According to some embodiments, while in the MRI mode stat therapy state 430, the IMD monitors for an MRI signal and/or a core saturation signal that indicates that the patient is no longer within the field of the MRI. When one of these signals is detected, the state control module 370 will cause the IMD to enter the normal operation mode 450. While in the normal operation mode 450, the IMD returns to full normal operation. If the arrhythmia still exists, the system can be configured to carry out all of its prescribed operations, including defibrillation shocks if programmed, to treat the arrhythmia by entering tachy therapy state 460.

In accordance with various embodiments, the tachy therapy state 460 can operate in a variety of different ways. For example, if a tachyarrhythmia episode remains from the MRI mode stat therapy state, the next therapy session can be a shock. In other cases, if the arrhythmia episode was successfully terminated after MRI mode stat therapy state 430 was exited, the next tachyarrhythmia therapy will be the programmed therapy.

According to various embodiments, tachyarrhythmia detection is restored when the patient is observed to be in distress. The MRI tech or operator terminates the MRI scan, causing the RF and gradient magnetic fields to cease. The MRI tech or operator may then send a stat therapy command from the external device to cause the IMD to enter the stat therapy mode. If the stat therapy command is sent, the IMD then enables the sensors and uses existing tachyarrhythmia detection to determine if an arrhythmia exists and if so, provides ATP and VVI pacing therapies, for example. As such, inadvertent stat therapy selection is benign to the patient since if no tachyarrhythmia is detected, no therapy will be applied.

Figure 5:
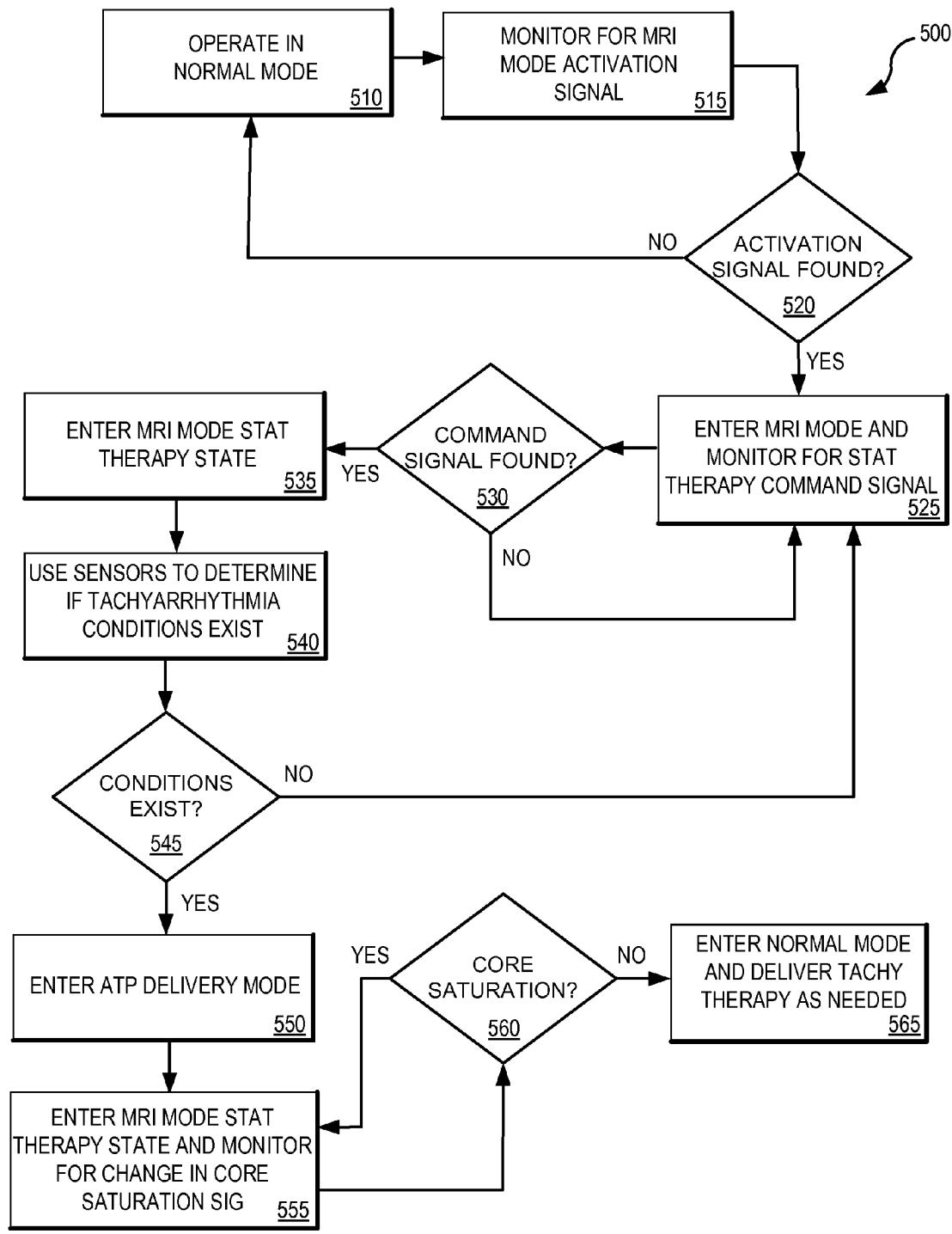
FIG. 5 is a flow chart illustrating exemplary operations of an implantable medical device in the presence of an MRI environment according to some embodiments of the present invention.

FIG. 5 is a flow chart 500 illustrating exemplary operations of an implantable medical device in the presence of an MRI environment according to some embodiments. According to various embodiments, the IMD is performing normal mode operations 510 with full IMD functionality. While in normal mode operations 510, the IMD is also performing monitoring operation 515 which monitors for an MRI activation signal. If no MRI activation signal is found, then MRI activation decision block 520 leaves the IMD in the normal mode operations 510. If, however, an activation signal is found at decision block 520, the IMD branches to enter MRI mode operation 525, which causes the IMD to enter the MRI mode.

In some embodiments, during MRI mode operation 525, the IMD monitors for a stat therapy command signal which originates from an external device. If during therapy command decision 530, no stat therapy command signal has been received, the IMD remains in MRI mode operation 525. If a stat therapy command signal has been received, therapy command decision 530 branches to enter the MRI mode stat therapy state 535. Tachyarrhythmia determination operation 540 then determines if a tachyarrhythmia condition exists using one or more IMD sensors.

At condition decision 545, if no tachyarrhythmia is present, the IMD returns to the MRI mode operation 525 in some embodiments. If a tachyarrhythmia is determined to be present, condition decision 545 branches to enter ATP delivery mode operation 550 where ATP pacing therapy is delivered. Once the pacing therapy is completed, the IMD enters MRI mode stat therapy state operation 555, causing the IMD to enter MRI mode stat therapy state. In addition, the IMD monitors for changes in a core saturation signal which indicates the presence of an MRI field. In some embodiments, the core saturation signal will only change after a fixed period (e.g., three seconds) of a detected change in the magnetic fields.

Core saturation decision 560 determines if the core saturation signal indicates the absence of an MRI field. If not, the IMD returns to MRI mode stat therapy state operation 555. If the core saturation signal indicates the absence of an MRI field, core saturation decision 560 branches to enter normal mode operation 565 which returns the IMD to normal operations.

Embodiments of the present invention may be provided as a computer program product which may include a machine-readable medium having stored thereon instructions which may be used to program a computer (or other electronic device) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for operating an implantable medical device (IMD) implanted within a patient in the presence of a magnetic resonance imaging (MRI) environment, the method comprising:

receiving a therapy command from an external device while the IMD is in the presence of an MRI electromagnetic field and is operating in a first operational mode in which one or more sensors of the IMD have been disabled, the therapy command configured to prompt the IMD to provide immediate therapy to the patient while in the MRI electromagnetic field; and placing the IMD in a second operational mode upon receiving the therapy command, wherein the second operational mode includes:

enabling the one or more sensors of the IMD;

determining whether a tachyarrhythmia is present using the one or more sensors; and delivering antitachycardia pacing (ATP) therapy to the patient if a tachyarrhythmia is determined to be present, wherein shock therapy is not delivered by the IMD when in the second operational mode if tachyarrhythmia is determined to be present while the IMD is in the presence of the MRI electromagnetic field.

2. The method of claim 1, wherein the second operational mode further comprises:

determining if the ATP therapy has been exhausted and if the tachyarrhythmia is still present; and delivering additional ATP therapy if the ATP therapy has not been exhausted and the tachyarrhythmia is determined to still be present.

3. The method of claim 1, further comprising:

monitoring for a core saturation signal that indicates the absence or presence of an MRI electromagnetic field that would result in an inability of the IMD to deliver tachyarrhythmia shock therapy; and placing the IMD in a third operational mode when the core saturation signal being monitored indicates the absence of the MRI electromagnetic field, wherein in the third operational mode the IMD is configured to determine if ATP therapy or shock therapy is needed and to deliver the ATP therapy or shock therapy when a determination is made that ATP therapy or shock therapy is needed.

4. The method of claim 1, further comprising:

monitoring a core saturation signal that indicates the absence of external magnetic fields that would interfere with tachyarrhythmia therapy delivered by the IMD;

if the core saturation signal indicates the absence of the external magnetic fields, placing the IMD in a third operational mode in which shock therapy is delivered if the deliver tachyarrhythmia is determined to be present therapy.

5. The method of claim 1, wherein the ATP therapy provides pacing at programmed intervals.

6. The method of claim 5, wherein providing ATP therapy at programmed intervals includes providing higher pacing rates in earlier programmed intervals and lower pacing rates in one or more subsequent intervals.

7. The method of claim 5, wherein the ATP therapy terminates after two or more programmed intervals.

8. The method of claim 1, wherein the IMD delivers no ATP therapy to the patient if a tachyarrhythmia is not sensed by the one or more sensors.

9. The method of claim 1, wherein the command is received from an operator via an external device.

10. The method of claim 1, wherein the one or more sensors have been disabled by either deactivating the one or more sensors or the output from the one or more sensors is being ignored by the IMD, and wherein enabling the one or more sensors of the IMD includes activating a deactivated sensor or monitoring the output from the one or more sensors that is being ignored.

11. An implantable medical device (IMD) configured for implantation in a patient to monitor cardiac activity in, and deliver therapy to, the patient's heart, the IMD comprising:
   a pulse generator operable to deliver pacing pulses and shock pulses;
   at least one lead having a proximal section coupled to the pulse generator and a distal section secured to the patient's heart, wherein the at least one lead is configured to deliver a therapeutic stimulus to the patient's heart; and
   a state control module operable to selectively place the IMD in any of a plurality of operational modes for operation of the IMD in the presence of an MRI electromagnetic field that is strong enough to interfere with operation of the IMD, wherein the IMD is configured to not deliver the shock pulses while in the presence of the MRI electromagnetic field and the operational modes include:
      a first operational mode where the IMD monitors for a therapy command from an external device indicating the need for immediate therapy, wherein the IMD is configured to not deliver the pacing pulses while in the first operational mode,
      a second operational mode that activates one or more sensors to be used in determining the presence of a tachyarrhythmia, wherein the IMD is configured to enter the second operational mode based on reception of the therapy command while in the first operational mode, and
      a third operational mode in which the IMD delivers the pacing pulses until the tachyarrhythmia is no longer determined to be present or until a fixed number of pacing sessions have been exhausted, wherein the IMD is configured to enter the third operational mode based on detecting the presence of the tachyarrhythmia in the second operational mode.

12. The IMD of claim 11, further comprising a communication module operable to receive mode commands from a device external to the patient, wherein the mode commands prompt the IMD to enter into the plurality of operational modes.

13. The IMD of claim 12, wherein the communication module includes circuitry for communicating wirelessly with the device external to the patient.

14. The IMD of claim 11, wherein the state control module is operable to place the IMD in a fourth operational mode while not in the presence of the MRI electromagnetic field, the IMD configured to monitor for tachyarrythmia and deliver shocks based on detection of tachyarrythmia while in the fourth operational mode.

15. The IMD of claim 14, wherein the IMD includes a communication module to receive and process command signals from the external device, and wherein the IMD will transition from the fourth operational mode and to the first operational mode after a first operational mode command signal is received.

16. The IMD of claim 14, wherein the IMD further includes an MRI detection module configured to automatically detect the presence of the MRI electromagnetic field, and wherein, in response to the detection of the MRI electromagnetic field, the state control module is configured to place the IMD in the first operational mode.

17. The IMD of claim 11, wherein, in the third operational mode, the IMD is configured to deliver pacing pulses up to a fixed number of pacing sessions.

18. A method of operating an implantable medical device (IMD) in the presence of a magnetic resonance imaging (MRI) environment, the method comprising:
   monitoring for an MRI signal indicating the presence of a strong MRI electromagnetic field that could interfere with operation of the IMD;
   entering a first operational mode when the MRI signal is detected, wherein upon entering the first operational mode of the IMD at least one sensor input to the IMD is ignored and no pacing therapy or shock therapy is delivered to a patient's heart;
   monitoring for a therapy command signal from an external device indicating the need for immediate therapy while the IMD is still in the presence of the MRI electromagnetic field and in the first operational mode;
   transitioning the IMD into a second operational mode upon detecting the therapy command signal while the IMD is still in the presence of the MRI electromagnetic field, wherein the at least one sensor input of the IMD is monitored to determine if a tachyarrhythmia exists while the IMD is in the second operational mode; and
   while the IMD is still in the second operational mode, delivering pacing therapy to the patient if a tachyarrhythmia is determined to be present while the IMD is still in the presence of the MRI electromagnetic field, wherein shock therapy is not delivered by the IMD if tachyarrhythmia is determined to be present while the IMD is still in the presence of the MRI electromagnetic field.

19. The method of claim 18, wherein the MRI signal is received from an external device.

20. The method of claim 18, wherein upon entering into the second operational mode, the method further comprises:
   monitoring for a core saturation signal which indicates a continued presence of the MRI electromagnetic field; and
   wherein delivering pacing therapy to the patient includes delivering up to a fixed number of antitachycardia pacing (ATP) therapy sessions if the tachyarrhythmia is determined to exist and the core saturation signal indicates the presence of the MRI electromagnetic field.

21. The method of claim 20, wherein once the core saturation signal indicates an absence of the MRI electromagnetic field, the method further comprises entering a third operational mode that allows the IMD to provide shock therapy to the patient.

* * * * *

UNITED STATES PATENT AND TRADEMARK OFFICE
CERTIFICATE OF CORRECTION

Page 1 of 1

PATENT NO. : 8,639,331 B2
APPLICATION NO. : 12/639848
DATED : January 28, 2014
INVENTOR(S) : Scott R. Stubbs, James O. Gilkerson and Diane Schuster It is certified that error appears in the above-identified patent and that said Letters Patent is hereby corrected as shown below:

In the Claims

Column 10, line 60: delete "deliver"
Column 10, line 61: delete "therapy"

Signed and Sealed this
Eighth Day of July, 2014

Michelle K. Lee
*Deputy Director of the United States Patent and Trademark Office*